United States Patent [19]
Reifschneider

[11] 4,439,431
[45] Mar. 27, 1984

[54] O,O-DIETHYL O-((4-TERTIARYBUTYLSULFONYL)M-TOLYL)PHOSPHOROTHIOATE AND ITS INSECTICIDAL USE

[75] Inventor: Walter Reifschneider, Walnut Creek, Calif.

[73] Assignee: The Dow Chemical Company, Midland, Mich.

[21] Appl. No.: 307,980

[22] Filed: Oct. 2, 1981

[51] Int. Cl.$^3$ ...................... A01N 57/14; C07F 9/165
[52] U.S. Cl. ...................................... 424/216; 260/949
[58] Field of Search ......................... 260/949; 424/216

[56] References Cited

U.S. PATENT DOCUMENTS 3,042,703 7/1962 Schegk et al. ...................... 260/949
3,351,682 11/1967 Baker et al. ........................ 260/949
4,065,558 12/1977 Gordon ............................... 424/216

FOREIGN PATENT DOCUMENTS 1183494 12/1964 Fed. Rep. of Germany .

OTHER PUBLICATIONS

Unverified Translation of Japanese Patent, 11880/66.

Primary Examiner—Anton H. Sutto
Attorney, Agent, or Firm—S. Preston Jones; Ronald G. Brookens

[57] ABSTRACT

O,O-Diethyl O-(4-(t-butylsulfonyl)-m-tolyl) phosphorothioate is an active insecticide for the kill and control of the copper bottle fly and the southern cattle tick.

4 Claims, No Drawings

O,O-DIETHYL O-((4-TERTIARYBUTYLSULFONYL)M-TOLYL)-PHOSPHOROTHIOATE AND ITS INSECTICIDAL USE

BACKGROUND OF THE INVENTION

Many phosphate and phosphorothioate esters are known to have pesticidal activity of one kind or another. Various related sulfur-substituted phosphorothioate esters are also known to be active insecticides and miticides. A number of such esters are described in U.S. Pat. No. 3,042,703, West German Patent No. 1,183,494, and Japanese Patent No. 11880/66. These patents all disclose esters having the general structural formula

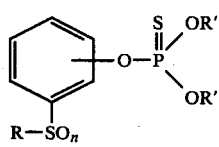

where the phenyl group may have one or more inert substituents, R' is a lower alkyl group, usually methyl or ethyl, R is also a lower alkyl group, and n is zero, one, or two. No compounds are shown where R is a tertiary alkyl group.

SUMMARY OF THE INVENTION

It has now been found that exceptional and different insecticidal activity exists for the compound O,O-diethyl O-[(4-tertiarybutylsulfonyl)m-tolyl] phosphorothioate which corresponds to the formula

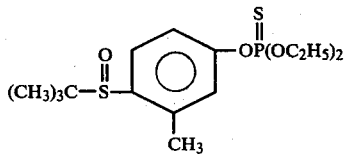

The present invention comprises the above-defined compound, insecticidal formulations containing the compound, and the use of such formulations for killing and controlling the copper bottle fly and southern cattle tick (*Boophilus microplus*).

DETAILED DESCRIPTION

The compounds of the present invention are useful as insecticides in a variety of household, industrial and agricultural operations, for the kill and control of both the copper bottle fly and the southern cattle tick.

When applied to animals, animal parts and their habitats to protect the animals from the attack of the copper bottle fly and southern cattle tick, the subject compounds exhibit good residual control of the insects.

The method of the present invention comprises contacting the insects with an insecticidally effective or inactivating amount of the compound of the present invention. The contacting can be effected by application of the compound to the insect or its habitat. The inactivation can be lethal, immediately or with delay, or can be a sublethal one in which the inactivated insect is not able to carry out one or more of its normal like processes. This latter situation prevails when one of the systems of the insect, typically the nervous system, is seriously disturbed.

The inactivation of an insect by the application of an insecticidally effective or inactivating amount of the compound is critical to the method of the present invention. The compound can be employed in unmodified form, or modified by the addition of a pesticidal adjuvant thereto.

Compositions employing one or a combination, the active compound can be in the form of a liquid or a dust; and the adjuvant employed can be any one of a plurality of materials including aromatic solvents, petroleum distillates, water, or other liquid carriers, propellent substances, surface-active dispersing agents, light absorbers, and finely divided carrier solids. In such compositions, the adjuvant cooperates with the phosphorus compound so as to obtain a composition to facilitate the method of the present invention, and to obtain an improved result. The use of either a surface-active dispersing agent and a finely divided carrier solid, simultaneously constitute preferred embodiments of the method of the present invention.

Another preferred embodiment of the present invention is a composition comprising the compound, an organic liquid as a solvent and carrier therefor, and a propellent material. Numerous other embodiments will become available to those skilled in the art in view of the teachings set forth hereinbelow.

The exact concentration of the compound of the present invention in a composition thereof with an adjuvant therefor can vary; it is only necessary that the compound be present in a sufficient amount so as to make possible the application of an insecticidally effective or inactivating concentration. A preferred spray concentration is from about 25 to about 500 ppm. Generally, for practical applications, the active compound(s) can be broadly applied to the insects or their habitat in compositions containing from about 0.00001 to about 98 percent by weight of the phosphorus compound(s).

In the preparation of dust compositions, the compound can be compounded with any of the finely divided carrier solids such as pyrophyllite, diatomaceous earth, gypsum and the like. In such operations, the finely divided carrier is ground or mixed with the compound, as active agent or wetted with a solution of the active agent in a volatile organic solvent. Similarly, dust compositions containing the phosphorus compound can be compounded with various solid dispersing agents, such as fuller's earth, attapulgite and other clays. These dust compositions can be employed as treating compositions or can be employed as concentrates and subsequently diluted with additional solid dispersing agent or with pyrophyllite, diatomaceous earth, gypsum and the like to obtain the desired amount of active agent in a treating composition. Also, such dust compositions can be dispersed in water, with or without the aid of surfactant, to form spray mixtures.

Furthermore, the compound or a dust concentrate composition containing the compound can be incorporated in intimate mixture with surface-active dispersing agents, such as ionic and nonionic emulsifying agents to form spray concentrates. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

In the preparation of liquid compositions, the compound can be compounded with a suitable water-immiscible organic liquid and surface active dispersing agent to produce an emulsifiable liquid concentrate which can be further diluted with water and oil to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil-soluble and include the nonionic emulsifiers such as polyoxyethylene derivatives or sorbitan esters, complex ether alcohols and the like. However, oil-soluble ionic emulsifying agents such as mahogany soaps can also be used. Suitable organic liquids to be employed in the compositions include petroleum oils and distillates, toluene, liquid halohydrocarbons and synthetic organic oils.

When operating in accordance with the present invention, the compound or a composition containing one or more of the products is applied to the insects to be controlled directly, or by means of application to their habitat in any convenient manner. The present invention also comprehends the employment of compositions comprising the phosphorus compound, an adjuvant, and one or more biologically active materials, such as other insecticides, fungicides, miticides, bactericides, nematocides, and the like.

The 4-(tertiarybutylsulfonyl)-m-cresol intermediate employed for making the compound of this invention are readily prepared from known compounds by conventional means. A preferred method comprises reacting 2-chloro-4-mercaptophenol with tertiary butyl alcohol or tertiary amyl alcohol at about 50°-100° C. in inert solvent solution in the presence of sulfuric or phosphoric acid to produce the 4-(t-butylthio)-2-chlorophenol. That product is readily isolated by adding water to the reaction mixture and separating the product from the organic layer thereby formed by conventional means.

This 4-(t-butylthio)-m-cresol can then be oxidized to the corresponding sulfonyl phenol by reacting it with an excess amount of any convenient oxidizing agent under conventional oxidizing reaction conditions. Suitable oxidizing agents include nitric acid, hydrogen peroxide, and benzoyl peroxide. A mode of oxidation using chlorine water to convert alkylthioaromatics to corresponding alkylsulfinyl compounds is described in U.S. Pat. No. 3,415,832.

A more convenient method comprises the use of 30% $H_2O_2$ to oxidize the alkylthiocresol in glacial acetic acid at reflux temperature, using a 50-75% excess of the theoretically required two moles of peroxide to make the desired alkylsulfonylcresol.

The O,O-diethyl phosphorochloridothioate intermediate reacted with the phenolic reactant to make the esters of this invention is a commercially available material.

EXAMPLE 1

O,O-Diethyl O-(4-(t-butylsulfonyl)-m-tolyl) phosphorothioate

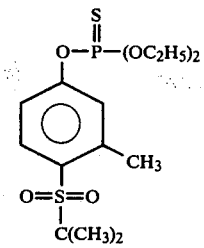

A mixture of 34.2 grams (0.15 mole) of 4-(t-butylsulfonyl)-m-cresol, 24 grams of powdered potassium carbonate, 200 milliliters of acetonitrile and 30 grams (0.16 mole) of O,O-diethyl phosphorochloridothioate was stirred and heated at approximately 50° C. until no starting phenol could be detected by GLC. For this, 3 hours were required. The insoluble salts, formed during the reaction, were removed by filtration and the filtrate was concentrated under reduced pressure. The oil which remained as a residue was dissolved in methylene chloride and the resulting solution was washed twice with water and dried over anhydrous sodium sulfate. The solvent was removed in a rotary evaporator, leaving 50 grams of O,O-diethyl O-(4-t-butylsulfonyl)-m-tolyl) phosphorothioate product (88 percent of theoretical) melting at 42°-44° C. The product crystallized upon standing and was recrystallized from hexane leaving white crystals with a melting point of 42°-44° C. The structure of the product was confirmed by NMR upon analysis, the product was found to have carbon and hydrogen contents of 47.13 and 6.71 respectively, as compared to the theoretical contents of 47.35 and 6.62 respectively calculated for the above product.

EXAMPLE 2

Predetermined amounts of O,O-diethyl O-[(4-tertiarybutylsulfonyl)-m-tolyl] phosphorothioate, in the form of a silica gel admixture, was mixed with predetermined amounts of acetone. The solutions thus prepared were absorbed onto cotton rolls, produced as No. 2 dental plugs. At the same time additional rolls were treated with silica gel and acetone, alone to serve as controls. The rolls were ¾ inch long and 2 such rolls were placed side by side in 0.625 ounce (5 dram) glass vials. The treated rolls were allowed to air dry for 24 hours so that the acetone could evaporate off. One cubic centimeter of bovine serum was placed on the cotton rolls in each vial. Thereafter, 50-100 1st stage copper bottle fly maggots of 1-6 hours of age were placed on the rolls in each vial. The vials were plugged with cotton and held for 24 hours at 82°-84° F. and 80 percent relative humidity. At the end of this period, the vials were examined to determine the percent kill and control of the maggots. It was found that the compound gave 100 percent kill and control of the copper bottle fly maggots when employed at 0.25 parts of the compound per million parts of the ultimate admixture (PPM).

EXAMPLE 3

In another operation, the compound was found to give 100 percent kill and control of southern cattle tick when applied thereto in an aqueous dispersion containing the compound as the sole toxicant, at 500 milligrams per 100 cubic centimeters of the ultimate dispersion.

I claim:

1. A method for killing and controlling the copper bottle fly which comprises contacting said fly or their habitat with a composition containing, as an active ingredient, an insecticidally effective amount of O,O-diethyl O-(4-(t-butylsulfonyl)-m-tolyl) phosphorothioate in intimate admixture with an inert carrier therefor.

2. A method for killing and controlling the southern cattle tick which comprises contacting said tick or their habitat with a composition containing, as an active ingredient, an insecticidally effective amount of O,O-diethyl O-(4-(t-butylsulfonyl)-m-tolyl) phosphorothioate in intimate admixture with an inert carrier therefor.

3. The compound O,O-diethyl O-(4-(t-butylsulfonyl)-m-tolyl) phosphorothioate.

4. An insecticidal composition comprising, as an active ingredient, an insecticidally effective amount of O,O-diethyl O-(4-(t-butylsulfonyl)-m-tolyl) phosphorothioate in intimate admixture with an inert carrier therefor.

* * * * *